United States Patent [19]
Harris

[11] Patent Number: 4,796,642
[45] Date of Patent: Jan. 10, 1989

[54] PACING LEAD STYLET

[75] Inventor: Donald L. Harris, Key Largo, Fla.

[73] Assignee: Cordis Leads, Inc., Miami, Fla.

[21] Appl. No.: 138,434

[22] Filed: Dec. 28, 1987

[51] Int. Cl.$^4$ .............................................. A61B 5/00
[52] U.S. Cl. .................................. 128/772; 128/657; 604/171
[58] Field of Search ............... 128/657, 772, 785, 786, 128/348.1; 604/95, 164, 166, 170, 171

[56] References Cited

U.S. PATENT DOCUMENTS

| | | | |
|---|---|---|---|
| 2,024,982 | 12/1935 | Scott | 128/348.1 |
| 3,906,938 | 9/1975 | Fleischhacker | 128/772 |
| 4,271,847 | 6/1981 | Stokes | 128/786 |
| 4,374,527 | 2/1983 | Iversen | 128/786 |
| 4,454,888 | 6/1984 | Gold | 128/786 |
| 4,456,017 | 6/1984 | Miles | 128/772 |
| 4,498,482 | 2/1985 | Williams | 128/786 |
| 4,538,622 | 9/1985 | Samson et al. | 128/657 |
| 4,545,390 | 10/1985 | Leary | 128/772 |
| 4,548,206 | 10/1985 | Osborne | 128/772 |
| 4,554,929 | 11/1985 | Samson et al. | 128/657 |
| 4,616,653 | 10/1986 | Samson et al. | 128/657 |
| 4,676,249 | 6/1987 | Arenas et al. | 128/772 |
| 4,721,117 | 1/1988 | Mar et al. | 128/772 |

Primary Examiner—Max Hindenburg
Attorney, Agent, or Firm—Henry W. Collins; Thomas R. Vigil

[57] ABSTRACT

The pacing lead stylet includes a proximal end, a stylet wire, a decreasing taper, a flat, an increasing taper and a tip. The decreasing taper is connected to the stylet wire and extends in a distal direction away from the wire distal end for a decreasing taper distance. The decreasing taper has a decreasing cross section which is reduced from the stylet cross sectional area to a decreased cross sectional area at a decreasing taper distal end of the decreasing taper. The flat is connected to the decreasing taper and extends in a distal direction away from the decreasing taper distal end for a flat distance to a flat distal end. The increasing taper is connected to the flat and extends in a distal direction away from the flat distal end for an increasing taper distal. The increasing taper has an increasing cross section from the minimum extension to the stylet cross section area. The tip is connected to the increasing taper extends in a distal direction away from the increasing taper for a predetermined distance, preferably equal to at least three pitch distances of a helical coil of the pacing lead. The tip has a generally constant tip cross section area except at a tip distal end which is hemispherical. The tip distal end has a maximum hemispherical cross section area nearly equal to the tip cross section area, and has a hemispherical radius of curvature larger than half a maximum tip cross section.

19 Claims, 1 Drawing Sheet

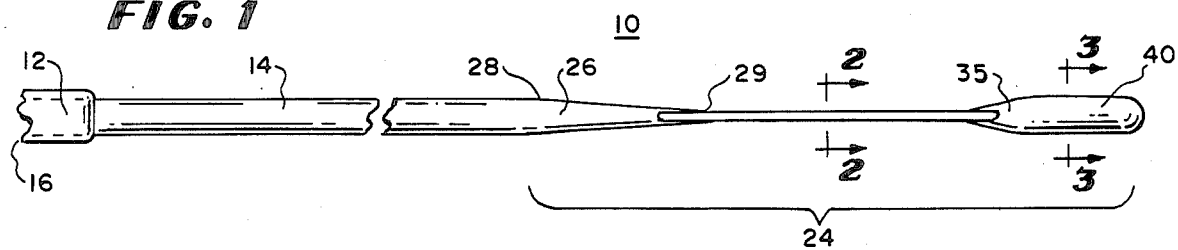
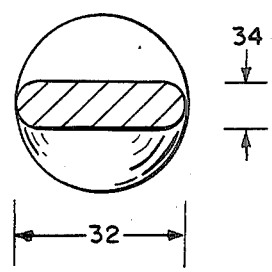
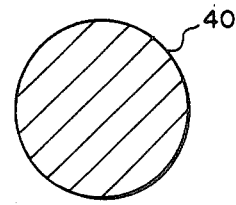
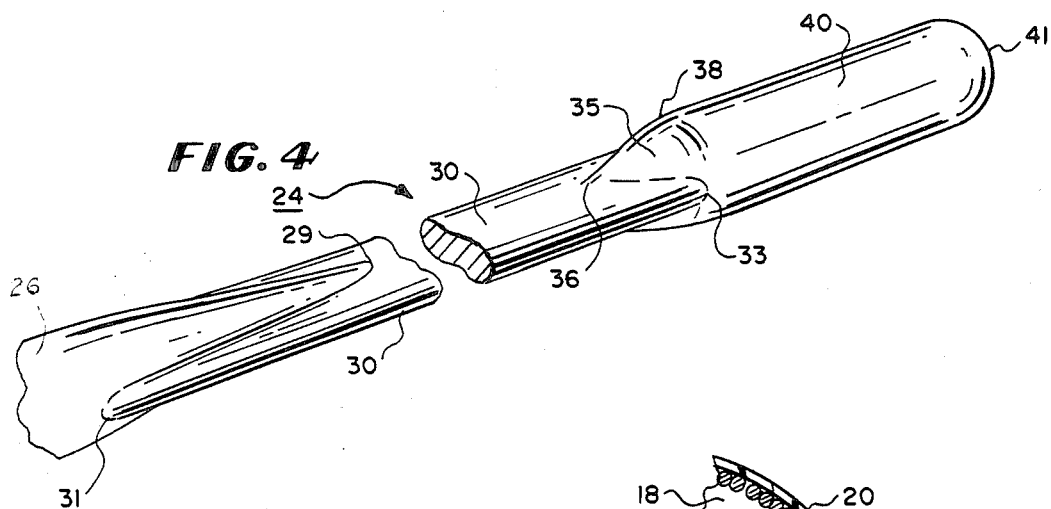
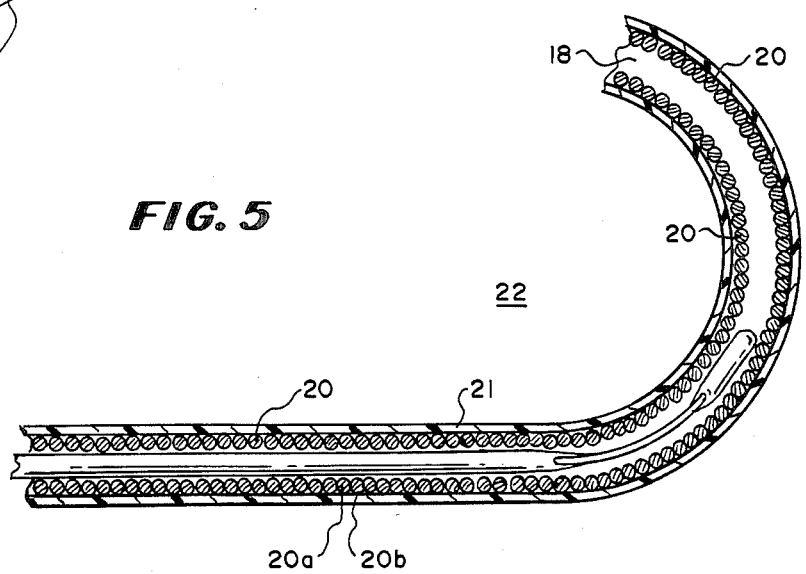

PACING LEAD STYLET

BACKGROUND OF THE INVENTION

1. Field of the Invention

The present invention relates to stylets and particularly relates to stylets used to implant pervenous leads.

2. Description of the Prior Art

A pacing lead stylet is normally used in the implantation of a pervenous pacing lead. The pervenous pacing lead is generally constructed of one or more coils of a wire conductor in an insulating sheath surrounding and defining a lumen. The distal end or that portion of the pervenous lead to be placed in the cavity of the heart has an electrode or electrodes affixed to the lead and electrically connected to the helically coiled wire conductors. The proximal end of the pervenous lead has a terminal assembly. The terminal assembly includes terminals electrically connected to the helically coiled wire conductor. This terminal assembly is adapted to be placed in a socket in the neck of an implanted cardiac pacer.

The helically coiled construction of the pervenous lead renders the lead most difficult to pass through an appropriate vein to the appropriate cavity of the heart. A stylet, when inserted into the lumen, imparts some rigidity to the lead enabling the physician to exert some force on the lead. However, a stylet with an unprotected distal tip can penetrate between the helical coils. Penetration is most likely in those patients having a tortuous vein, and is potentially injurious to both the performance of the lead, and the patient.

Further, there are pervenous leads which have a preformed curve. One such lead is the atrial "J" lead, in which there is a rather pronounced curve. Since precurved leads must be straightened for placement, with available stylets difficulties are encountered such as penetration between coils or the catching of the stylet tip on a coil.

There have been a number of proposals for stylet constructions which reduce the risk of penetration while providing sufficient rigidity for pervenous leads and related devices.

U.S. Pat. No. 4,548,206 to Osborne discloses a CATHETER WIRE GUIDE WITH MOVABLE MANDRIL. The movable mandril is tapered towards its distal end which is an elongate bulb.

U.S. Pat. No. 4,554,929 to Samson et al. discloses a CATHETER GUIDE WIRE WITH SHORT SPRING TIP AND A METHOD OF USING THE SAME. The spring tip surrounds a reduced section extension of a guidewire shaft.

U.S. Pat. No. 4,498,482 to Williams discloses a TRANSVENOUS PACING LEAD HAVING IMPROVED STYLET. The stylet has a constant diameter at its proximal end, a ball at its distal end and a tapered section in the transition of the stylet from a constant diameter to the ball portion. This pacing lead stylet has a ball placed on the distal end of the stylet to prevent penetration between the coils. However, the ball on such a stylet can get caught by one of the coils preventing its advancement or withdrawal within the lumen of the pervenous lead.

The non-analogus U.S. Pat. No. 4,456,017 to Miles discloses a COILED SPRING GUIDE WITH DEFLECTABLE TIP. Its core wire has a reduced section at its distal end which is permanently, and eccentrically, affixed to a head member. Proximal movement of the core wire causes the guide to assume an arcuate shape.

U.S. Pat. No. 4,454,888 to Gold discloses a CARDIAC PACING LEAD WITH CURVE RETAINER. A flat spring near its distal end causes the lead to assume a J-shape when a stylet is withdrawn from that portion of the lead.

U.S. Pat. No. 4,271,847 to Stokes discloses a TEMPORARY ADJUSTABLE BIPOLAR LEAD including a coaxial sliding pacing lead for establishing a connection between a chamber of a heart and a pulse generator.

The non-analogus U.S. Pat. No. 3,906,938 to Fleischhacker discloses a COIL SPRING WIRE GUIDE including a coil spring surrounding a core wire which is welded to a spring tip. The core wire is substantially cylindrical except in its distal portion where it is flattened adjacent its joinder to the spring tip.

The non-analogus U.S. Pat. No. 2,024,982 to Scott discloses a SURGICAL INSTRUMENT including a stylet having a flat, tapered stylet portion near an ellipoidal shaped tip.

United Kingdom Patent Application No. 2 064 963 A describes a STYLET having a tapered portion terminating at a ball in its distal end and corresponds to U.S. Pat. No. 4,498,482 referred to above.

Swedish Patent No. 193885 discloses A CATHETER INTENDED FOR INTRAVASCULAR CATHETERIZATION having an arcuately curved distal end which is straightenable by an inserted stylet. The stylet has a rounded cylindrical distal end portion.

The non-analogus prior art patents are not considered to be citable prior patents with respect to the claimed stylet and are only being cited herein to comply with the duty of disclosure.

Moreover, none of the foregoing patent publications disclose a pacing lead stylet which completely addresses concerns about penetration while having a selective balance between rigidity and flexibility to be usable with both straight and precurved pacing leads.

SUMMARY OF THE INVENTION

According to the invention, there is provided a pacing lead stylet for inserting a pervenous pacing lead into a patient. The pervenous pacing lead includes at least one helical coil in an insulating sheath surrounding a lumen. The lumen is open at a proximal end of the pacing lead and extends to a distal end of the pacing lead where it is generally closed by a pacing lead electrode assembly. The helical coil has a specific pitch distance between adjacent turns. The stylet includes a proximal end, a stylet wire, a decreasing taper, a flat, an increasing taper and a tip. The proximal end is adapted for manipulation of the stylet axially and rotationally within the pacing lead. The stylet wire is connected to the proximal end and extends in distal direction from the proximal end and for an axial length sufficient to nearly contact the pacing lead electrode assembly with a wire distal end of the stylet wire, when the stylet wire is fully inserted into the sheath lumen. The stylet wire has a generally constant stylet cross sectional area. The decreasing taper is connected to the stylet wire and extends in a distal direction away from the wire distal end for a decreasing taper distance. The decreasing taper has a decreasing cross section which is reduced from the stylet cross sectional area to a decreased cross sectional area at a decreasing taper distal end of the decreasing taper. The flat is connected to the decreasing taper and extends in a distal direction away from the decreasing taper distal end for a flat distance to a flat distal end. The flat has a cross section which has a maximum extent and a minimum extent. The increasing taper is connected to the flat and extends in a distal direction away from the flat distal end for an increasing taper distance. The increasing taper has an increasing cross section from the minimum extent to the stylet cross section area. The tip is connected to the increasing taper and extends in a distal direction away from the increasing taper. The tip has a generally constant tip cross section area except at a tip distal end which is hemispherical. The tip distal end has a maximum hemispherical cross section area nearly equal to the constant tip cross section area, and has a hemispherical radius of curvature larger than half a maximum tip cross section.

The tip is sufficiently long to encompass several coils, preferably three pitch distances. The flat or flattened portion of the stylet wire allows the stylet to traverse around a curve in a "J" lead. The decreasing taper overlaps the flat and extends for a sufficient length to permit a gradual straightening of the preformed curve of a "J" lead thereby spreading the straightening forces over a comparatively long taper overlapping and extending proximally of the flat and preventing excessive forces on the lead. The decreasing taper and the "spring" of the flat prevent the tip from "hanging up". "Hanging up" is also prevented by having the width of the flat substantially the same as the width of the stylet wire and of the tip.

BRIEF DESCRIPTION OF THE DRAWING

FIG. 1 is a side plan view of the pacing lead stylet constructed according to the teachings of the present invention.

FIG. 2 is a cross section of the pacing lead stylet shown in FIG. 1 and is taken along line 2—2 of FIG. 1.

FIG. 3 is a cross section of the pacing lead stylet shown in FIG. 1 and is taken along line 3—3 of FIG. 1.

FIG. 4 is a fragmentary perspective view of tapered and flattened portions of the pacing lead stylet shown in FIG. 1 with portions broken away.

FIG. 5 is a longitudinal sectional view of a portion of a J shaped pacing lead with the distal end portion of the pacing stylet received therein.

DESCRIPTION OF THE PREFERRED EMBODIMENT

A pacing lead stylet 10 is illustrated in FIG. 1. The pacing lead stylet 10 has a knurled handle 12 and a stylet wire 14. The knurled handle 12 is part of the proximal end 16 of the pacing lead stylet 10. This handle 12 facilitates the manipulation of the pacing lead stylet by the physician.

The knurled handle 12 at the proximal end 16 of the stylet does not enter a lumen 18 which forms the interior of a coiled wire conductor 20 surrounded by an insulating sheath 21 of a pervenous lead 22 shown in FIG. 5. The stylet wire 14 is sufficiently long to nearly extend the entire length of the pervenous pacing lead 22 shown in FIG. 5. Adjacent coils 20a and 20b of the coiled wire conductor 20 have a pitch distance between them. The diameter of the stylet wire 14 is approximately 0.014 inches and the wire 14 is essentially isodiametric throughout much of its length.

However a distal region 24 of stylet 10 is not isodiametric. The distal region 24 encompasses less than one inch of the entire stylet 10.

The stylet wire 14 joins a decreasing taper 26 at a point 28. This taper 26 extends for a decreasing taper distance to a decreasing taper distal end 29. Decreasing taper 26 is generally conical and decreasing in diameter, and cross section area, from that of stylet wire 14 to a decreased diameter, and cross section area, along the decreasing taper distance. The preferred decreasing taper distance is a minimum of 0.100 inches.

A flat 30 is connected to decreasing taper 26 adjacent decreasing taper distal end 29. This flat 30 of the stylet is flattened by grinding or making use of a die and extends for a flat distance. A maximum extent 32 of the cross section of flat 30 of the stylet 10 (FIG. 2) is the same dimension, that is 0.014 inches, in this preferred embodiment, as the diameter of the isodiametric stylet wire 14. However, the minimum extent 34 is equal to the decreased diameter of the decreasing taper 26 and is approximately 0.004 inches. The flat distance is about 0.275 inches between flat proximal end 31 and flat distal end 33.

An increasing taper 35 is joined to the flat 30 near flat distal end 33. Increasing taper 35 is generally conical and increasing in diameter, and cross section area, from the minimum extent 34 to a diameter equal to the isodiametric section of the stylet wire 14. An increasing taper distance from increasing proximal end 36 of the increasing taper 35 to an increasing distal end 38, where it becomes isodiametric, is less than the decreasing taper distance of decreasing taper 26. Something less than half the decreasing taper distance will impart rigidity to this portion of stylet 10.

Flat 30 overlaps portions of the decreasing taper 26 and increasing taper 35 for about a third of their respective distances to provide a strong and smooth transition among them.

The isodiametric tip 40 is connected to increasing taper 35 at increasing taper distal end 38. The diameter of tip 40 is of the same diameter as the stylet wire 14 measured from the proximal end 16 to the beginning 28 of the decreasing taper 26 to a tip distal end 41. Tip distal end 41 is generally hemispheric and has a maximum cross section equal to that of tip 40. Preferably, the radius of curvature of the hemisphere is greater than that of tip 40. The isodiametric tip 40 has a tip distance of approximately 0.075 inches between increasing taper distal end 38 and tip distal end 41. The tip distance should be long enough to extend past several adjacent coils 20, when stylet 10 is within lumen 18 of lead 20.

In use, the stylet 10 is inserted into the lumen 18 of the pervenous lead 20. The stylet 10 is particularly useful in those pervenous leads which are precurved such as a J-lead which has a sharp curve 42 as shown in FIG. 5. The stylet 10 is advanced through the lumen 18. When passing through the curve 42 several coils or a small region of the coils are adjacent to the isodiametric tip 40 thereby reducing or eliminating the possibility of the stylet entering the insulation between two adjacent coils 20. The flat 30 is sufficiently flexible so that stylet 10 conforms to the preformed curve 42 of the pervenous lead 22 while allowing the decreasing taper 26 to straighten the preformed curve 42.

According to the teachings of the present invention, judicious rotation of the stylet 10 within the lumen 18 can impart selective varying effective stiffness to the stylet 10 in the region of the flat 30. The length of the decreasing taper 26 is such that there is a "gentle" straightening of the pervenous lead 22 preventing excessive forces form being exerted on the lead or on the lead tissue interface.

From the foregoing description it will be apparent that modifications can be made to the pacing lead stylet 10 of the present invention without departing from the teachings of the invention. Also, it will be appreciated that the stylet 10 has a number of advantages, some of which have been described above and others of which are inherent in the invention. Accordingly, the scope of the invention is only to be limited as necessitated by the accompanying claims.

I claim:

1. A pacing lead stylet for insertion into a pervenous pacing lead for facilitating insertion of the lead into a patient, the pervenous pacing lead including at least one helical coil in an insulating sheath surrounding a lumen, the lumen being open at a proximal end of the pacing lead and extending to a distal end of the pacing lead where it is generally closed by a pacing lead electrode assembly, said stylet comprising:
   a proximal end adapted for manipulation;
   a distal end;
   a stylet wire connected to said proximal end and extending in distal direction from the proximal end to said distal end and having an axial length sufficient to nearly contact the pacing lead electrode assembly with said stylet distal end, when said stylet wire is fully inserted into the lumen, said stylet wire having a generally constant stylet cross sectional area;
   a decreasing taper connected to said stylet wire and extending in a distal direction away from the wire distal end for a decreasing taper distance, said decreasing taper having a decreasing cross section which is reduced from the stylet cross sectional area to a decreased cross sectional area at a decreasing taper distal end of said decreasing taper;
   a flat connected to said decreasing taper and extending in a distal direction away from the decreasing taper distal end for a flat distance to a flat distal end, said flat having a cross section which has a maximum extent and a minimum extent;
   an increasing taper connected to said flat and extending in a distal direction away from said flat distal end for an increasing taper distance, said increasing taper having an increasing cross section from the minimum extent of the flat to the stylet cross section area; and
   a tip at said stylet distal end connected to said increasing taper extending in a distal direction away from said increasing taper for a predetermined distance, said tip having a generally constant tip cross section area except at a tip distal end which is hemispherical, has a maximum hemispherical cross section area nearly equal to the tip cross section area, and has a hemispherical radius of curvature larger than half a maximum tip cross section.

2. The pacing lead stylet of claim 1 wherein:
said decreasing taper, said flat and said increasing taper overlap for portions of their respective distances.

3. The pacing lead stylet of claim 2 wherein:
said flat overlaps the distal third of said decreasing taper, and overlaps the proximal third of said increasing taper.

4. The pacing lead stylet of claim 1 wherein:
said decreasing taper has a decreasing taper distance which is at least six times a maximum cross section of said stylet wire.

5. The pacing lead stylet of claim 4 wherein:
said decreasing taper, said flat and said increasing taper overlap for portions of their respective distances.

6. The pacing lead stylet of claim 5 wherein:
said flat overlaps the distal third of said decreasing taper, and overlaps the proximal third of said increasing taper.

7. The pacing lead stylet of claim 6 wherein:
said increasing taper has an increasing taper distance which is less than three times the maximum cross section of said stylet wire.

8. The pacing lead stylet of claim 7 wherein:
said flat has a flat distance which is about twenty times the maximum cross section of said stylet wire.

9. The pacing lead stylet of claim 8 wherein:
said stylet wire has a generally circular cross section;
said decreasing taper has a generally conical cross section with the cone apex at its distal end; and
said increasing taper has a generally conical cross section with the cone apex at a proximal end.

10. The pacing lead stylet of claim 9 wherein:
said flat has a maximum extent approximately equal to the diameter of said stylet wire.

11. The pacing lead stylet of claim 10 wherein:
said flat has a minimum extent approximately one third of the maximum extent.

12. The pacing lead stylet of claim 1 for use with a pacing lead having at least one helically coiled wire conductor with each coil or turn having a predetermined pitch, a specific pitch distance between turns, and wherein said tip has a length equal to at least three pitch distances.

13. A pacing lead stylet for insertion into a pervenous pacing lead for facilitating insertion of the lead into a patient, the pervenous pacing lead including at least one helical coil in an insulating sheath surrounding a lumen, the lumen being open at a proximal end of the pacing lead and extending to a distal end of the pacing lead where it is generally closed by a pacing lead electrode assembly, the helical coil having a specific pitch distance between adjacent turns, said stylet comprising:
   a proximal end adapted for manipulation;
   a distal end;
   a stylet wire connected to said proximal end and extending in distal direction from the proximal end and having an axial length sufficient to nearly contact the pacing lead electrode with said stylet distal end, when said stylet wire is fully inserted into the lumen, said stylet wire having a generally constant wire cross sectional area, and having a cross section wire maximum extent and a wire minimum extent;
   a decreasing taper connected to said stylet wire and extending in a distal direction away from the wire distal end for a decreasing taper distance, said decreasing taper having a decreasing cross section which is reduced from the stylet cross sectional area to a decreased cross sectional area at a decreasing taper distal end of said decreasing taper;
   a flat connected to said decreasing taper and extending in a distal direction away from the decreasing taper distal end for a flat distance to a flat distal end, said flat having a cross section which has a flat maximum extent and a flat minimum extent, the flat minimum extent being approximately one third of the wire maximum extent;

an increasing taper connected to said flat and extending in a distal direction away from said flat distal end for an increasing taper distance, said increasing taper having an increasing cross section from the flat minimum extent to the wire cross section area; and a tip connected to said increasing taper extending in a distal direction away from said increasing taper for a distance equal to at least three pitch distances said tip having a generally constant tip cross section area approximately equal to the wire cross sectional area except at a tip distal end which is hemispherical, has a maximum hemispherical cross section area nearly equal to the tip cross section area, and has a hemispherical radius of curvature larger than half a maximum tip cross section.

14. The pacing lead stylet of claim 13 wherein:
said decreasing taper has a decreasing taper distance which is at least six times the wire minimum extent.

15. The pacing lead stylet of claim 14 wherein:
said decreasing taper, said flat and said increasing taper overlap for portions of their respective distances.

16. The pacing lead stylet of claim 15 wherein:
said flat overlaps the distal third of said decreasing taper, and overlaps the proximal third of said increasing taper.

17. The pacing lead stylet of claim 16 wherein:
said increasing taper has an increasing taper distance which is less than two thirds the decreasing taper distance.

18. The pacing lead stylet of claim 17 wherein:
said flat has a flat distance which is about twenty times the maximum cross section of said stylet wire.

19. A pacing lead stylet for insertion into a pervenous pacing lead for facilitating insertion of the lead into a patient, the pervenous pacing lead including at least one helical coil in an insulating sheath surrounding a lumen, the lumen being open at a proximal end of the pacing lead and extending to a distal end of the pacing lead where it is generally closed by a pacing lead electrode assembly, the helical coil having a specific pitch distance between adjacent turns, said stylet comprising:

a proximal end adapted for manipulation;

a distal end;

a cylindrical stylet wire connected to said proximal end and extending in distal direction from the proximal end and having an axial length sufficient to nearly contact the pacing lead electrode assembly with said stylet distal end, when said stylet wire is fully inserted into the lumen, said stylet wire having a generally constant wire diameter;

a decreasing taper connected to said stylet wire and extending in a distal direction away from the wire distal end for a decreasing taper distance, said decreasing taper having a decreasing cross section which is reduced for the wire diameter to a decreased taper diameter at a decreasing taper distal end of said decreasing taper;

a flat connected to said decreasing taper and extending in a distal direction away from the decreasing taper distal end for a flat distance to a flat distal end, said flat having a cross section which has a flat maximum extent being approximately equal to the wire diameter and a flat minimum extent, the flat minimum extent being approximately one third of the wire diameter;

an increasing taper connected to said flat and extending in a distal direction away from said flat distal end for an increasing taper distance, said increasing taper having an increasing cross section from the flat minimum extent to the wire diameter; and a cylindrical tip connected to said increasing taper extending in a distal direction away from said increasing taper for a distance equal to at least three pitch distances said tip having a generally constant tip diameter approximately equal to the wire diameter except at a tip distal end which is hemispherical, has a maximum hemispherical cross section area nearly equal to the tip cross section area, and has a hemispherical radius of curvature larger than half the wire diameter.

* * * * *

UNITED STATES PATENT AND TRADEMARK OFFICE
CERTIFICATE OF CORRECTION

PATENT NO. : 4,796,642
DATED : January 10, 1989
INVENTOR(S) : Donald L. Harris

It is certified that error appears in the above-identified patent and that said Letters Patent is hereby corrected as shown below:

Column 6, line 28 "the diameter" should be --a diameter--

Column 8, line 17 "for the wire" should be --from the wire--

Signed and Sealed this

Fourth Day of December, 1990

Attest:

HARRY F. MANBECK, JR.

*Attesting Officer*    *Commissioner of Patents and Trademarks*